United States Patent
Cho et al.

(10) Patent No.: US 9,731,282 B2
(45) Date of Patent: Aug. 15, 2017

(54) LIGAND COMPOUND, ORGANIC CHROMIUM COMPOUND, CATALYST SYSTEM FOR ETHYLENE OLIGOMERIZATION, PREPARATION METHOD THEREOF, AND ETHYLENE OLIGOMERIZATION METHOD USING THE SAME

(71) Applicant: LG CHEM, LTD., Seoul (KR)

(72) Inventors: Min-Seok Cho, Daejeon (KR); Yong-Ho Lee, Daejeon (KR); Seok-Pil Sa, Daejeon (KR); Heon-Yong Kwon, Daejeon (KR); Kyung-Jin Cho, Daejeon (KR); Se-Young Kim, Daejeon (KR); Sung-Min Lee, Daejeon (KR); Ki-Soo Lee, Daejeon (KR); Kyoung-Chan Lim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/440,683

(22) PCT Filed: Apr. 12, 2013

(86) PCT No.: PCT/KR2013/003093
§ 371 (c)(1),
(2) Date: May 5, 2015

(87) PCT Pub. No.: WO2014/077472
PCT Pub. Date: May 22, 2014

(65) Prior Publication Data
US 2015/0298110 A1    Oct. 22, 2015

(30) Foreign Application Priority Data

Nov. 15, 2012  (KR) .................. 10-2012-0129560
Dec. 11, 2012  (KR) .................. 10-2012-0143840

(51) Int. Cl.
*C07C 2/00* (2006.01)
*B01J 31/22* (2006.01)
(Continued)

(52) U.S. Cl.
CPC ............ *B01J 31/22* (2013.01); *B01J 21/08* (2013.01); *B01J 21/12* (2013.01); *B01J 21/14* (2013.01);
(Continued)

(58) Field of Classification Search
CPC .... C08F 4/69267; C08F 4/69215; C08F 4/69; C08F 4/78
See application file for complete search history.

(56) References Cited

U.S. PATENT DOCUMENTS

| | | | |
|---|---|---|---|
| 7,511,183 B2 * | 3/2009 | Blann | B01J 31/143 502/103 |
| 2007/0185357 A1 * | 8/2007 | De Boer | B01J 31/143 585/511 |
| 2007/0185363 A1 * | 8/2007 | Bercaw | B01J 31/18 585/521 |

FOREIGN PATENT DOCUMENTS

| | | |
|---|---|---|
| CN | 1651142 A | 8/2005 |
| CN | 101415494 A | 4/2009 |

(Continued)

OTHER PUBLICATIONS

Monoi, T.; Sasaki, Y. J. Mol. Catal. A: Chemical 2002, 187, 135-141.*

(Continued)

*Primary Examiner* — Rip A Lee
(74) *Attorney, Agent, or Firm* — Dentons US LLP

(57) ABSTRACT

The present invention relates to a ligand compound, an organic chromium compound, a catalyst system for ethylene oligomerization, a preparation method thereof, and an eth- (Continued)

ylene oligomerization method using the same. The catalyst system for ethylene oligomerization according to the present invention is used to prepare a low-density polyethylene in one reactor by using a small amount of comonomers such as alpha-olefin or by using only ethylene without comonomers, because it maintains high catalytic activity and high alpha-olefin selectivity even though supported on a support.

19 Claims, 1 Drawing Sheet

(51) Int. Cl.
| | |
|---|---|
| B01J 31/18 | (2006.01) |
| C07F 9/46 | (2006.01) |
| C07F 11/00 | (2006.01) |
| C08F 10/02 | (2006.01) |
| B01J 21/08 | (2006.01) |
| B01J 21/12 | (2006.01) |
| B01J 21/14 | (2006.01) |
| B01J 31/14 | (2006.01) |
| B01J 37/02 | (2006.01) |
| C07C 2/32 | (2006.01) |
| C07F 9/28 | (2006.01) |
| C08F 110/02 | (2006.01) |
| B01J 31/16 | (2006.01) |

(52) U.S. Cl.
CPC ......... *B01J 31/143* (2013.01); *B01J 31/1616* (2013.01); *B01J 31/1805* (2013.01); *B01J 31/189* (2013.01); *B01J 31/1845* (2013.01); *B01J 31/1895* (2013.01); *B01J 31/2204* (2013.01); *B01J 37/0219* (2013.01); *C07C 2/32* (2013.01); *C07F 9/28* (2013.01); *C07F 9/46* (2013.01); *C07F 11/00* (2013.01); *C07F 11/005* (2013.01); *C08F 10/02* (2013.01); *C08F 110/02* (2013.01); *B01J 2231/20* (2013.01); *B01J 2531/62* (2013.01); *C07C 2531/14* (2013.01); *C07C 2531/18* (2013.01); *C07C 2531/22* (2013.01)

(56) References Cited

FOREIGN PATENT DOCUMENTS

| | | | | |
|---|---|---|---|---|
| CN | 103044181 A | * | 4/2013 | ........... C07C 11/107 |
| JP | 4266827 B2 | | 5/2009 | |
| KR | 10-2003-0017616 A | | 3/2003 | |
| KR | 10-2008-0068227 A | | 7/2008 | |
| KR | 10-2008-0080570 A | | 9/2008 | |
| KR | 10-2008-0112295 A | | 12/2008 | |
| KR | 10-2009-0017929 A2 | | 2/2009 | |
| KR | 10-2010-0046170 A | | 5/2010 | |
| KR | 10-1065596 B1 | | 9/2011 | |
| KR | 10-2012-0048468 A | | 5/2012 | |
| KR | 10-2012-0138309 A | * | 12/2012 | .............. B01J 31/16 |
| WO | WO 2005/123884 A1 | * | 12/2005 | ............. C10G 50/00 |
| WO | 2007/088329 A1 | | 8/2007 | |
| WO | 2008/004986 A1 | | 1/2008 | |
| WO | WO 2008/004986 A1 | * | 1/2008 | ............. C07C 11/02 |

OTHER PUBLICATIONS

Sa, S.; Lee, S. M.; Kim, S.Y. J. Mol. Catal. A: Chemical 2013, 378, 17-21.*
Aydemir, M.; Baysal, A.; Gumgum, B. J. Organomet. Chem. 2008, 693, 3810-3814.*
Elowe, P.; McCann, C.; Pringle, P.G.; Spitzmesser, S.K.; Bercaw, J.E. Organometallics, 2-6, 25, 5255-5260.*
Elove, P. R. et al.: "Nitrogen-Linked Diphosphine Ligands with Ethers Attached to Nitrogen for Chrominum-Catalyzed Etheylene Tri- and Tetra-merizations", Organometallics, 2006, vol. 25, pp. 5255-5260.
A. Carter, et al.: "High activity ethylene trimerisation catalysts based on diphosphine ligands", The Royal Society of Chemistry, Chem. Commun., 2002, pp. 858-859.
D. McGuinness, et al.: "First Cr(III)—SNS Complexes and Their Use as Highly Efficient Catalysts for the Trimerization of Ethylene to 1-Hexene", J. Am. Chem. Soc. 2003, vol. 125, pp. 5272-5273.
J. Zhang, et al.: "Effect of Catalysts Supporting on Tandem Polymerization of Ethylene Stock in Synthesis of Ethylene—1-Hexene Copolymer", Ind. Eng. Chem. Res., 2008, vol. 47, pp. 5369-5375.
Faught: "The Crystal and molecular structure of 1,1-bis(diphenylphosphino)-2,2-dimethylhydrazine", Can. J. Chem. 54, p. 738 (1976).
Weng, et al.: "Chromium(III) catalysed ethylene tetramerization promoted by bis(phosphino)amines with an N-functionalized pendant", Dalton Transactions: The International Journal for Inorganic, Organometallic and Bioinorganic Chemistry; Royal Society of Chemistry, GB, No. 32, Aug. 28, 2007, pp. 3493-3498.

* cited by examiner

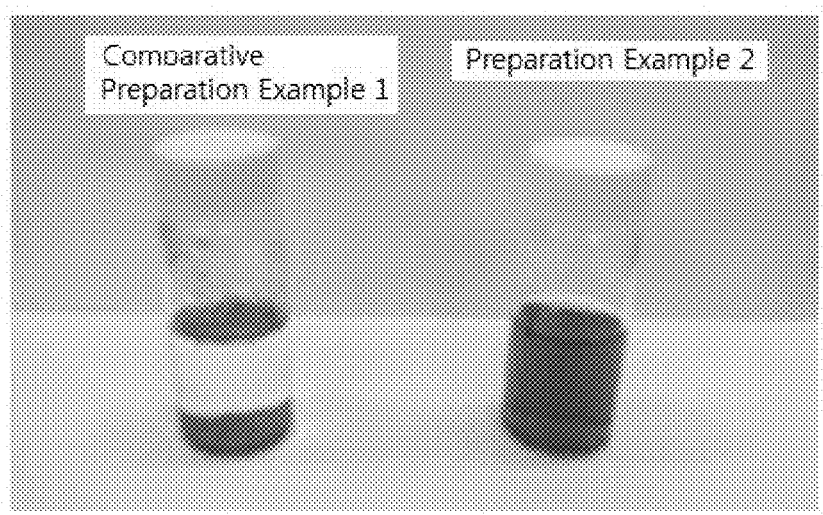

LIGAND COMPOUND, ORGANIC CHROMIUM COMPOUND, CATALYST SYSTEM FOR ETHYLENE OLIGOMERIZATION, PREPARATION METHOD THEREOF, AND ETHYLENE OLIGOMERIZATION METHOD USING THE SAME

This application is a National Stage Entry of International Application No. PCT/KR2013/003093, filed Apr. 12, 2013, which claims priority to and the benefit of Korean Application No. 10-2012-0129560, filed on Nov. 15, 2012 and Korean Patent Application No. 10-2012-0143840 filed on Dec. 11, 2012, all of which are hereby incorporated by reference in their entirety.

BACKGROUND OF THE INVENTION (a) Field of the Invention

The present invention relates to a ligand compound, an organic chromium compound, a catalyst system for ethylene oligomerization, a preparation method thereof, and an ethylene oligomerization method using the same. More particularly, the present invention relates to a ligand compound, an organic chromium compound, a catalyst system for ethylene oligomerization, a preparation method thereof, and an ethylene oligomerization method using the same, in which they can be used to prepare a low-density polyethylene in one reactor by using a small amount of comonomers or by using only ethylene without comonomers, and in particular, they maintain high catalytic activity and high alpha-olefin selectivity even though supported on a support.

(b) Description of the Related Art

Linear alpha-olefin is widely used in important commercial substances such as comonomers, detergents, lubricants, plasticizers or the like, and in particular, 1-hexene and 1-octene are used for polymerization of olefins having various physical properties by one catalyst.

They are commonly used as comonomers for controlling density of polyethylene during preparation of linear low density polyethylene (LLDPE).

In the conventional preparation process of LLDPE (Linear Low-Density Polyethylene), copolymerization of ethylene with alpha-olefin, for example, a comonomer such as 1-hexene and 1-octene is carried out in order to control density by forming branches in the polymer backbone.

Therefore, there is a problem that the comonomer increases the production cost of LLDPE having a high content of comonomers. Many different methods have been tried to solve this problem.

Further, because the application field or market size depends on the type of alpha-olefin, a technique capable of selectively producing a particular olefin is commercially important. Recently, many studies have been conducted on a chromium catalyst for preparing 1-hexene or 1-octene with a high selectivity through selective ethylene oligomerization.

The conventional commercial method for 1-hexene or 1-octene preparation is the SHOP process of Shell Chemical, the Ziegler process of Chevron Philips, or the like, which is used to produce alpha-olefins having a wide distribution ranging from 4 to 20 carbons.

A chromium-based catalyst for ethylene trimerization having a ligand of the formula $(R_1)(R_2)X$—Y—$X(R_3)(R_4)$ has been suggested, in which X is phosphorus, arsenic or antimony, Y is a linking group such as —$N(R_5)$—, and at least one of $R_1$, $R_2$, $R_3$ and $R_4$ has a polar substituent or an electron donating substituent.

Further, studies have been conducted on (o-ethylphenyl)$_2$PN(Me)P(o-ethylphenyl)$_2$ as a ligand which shows no catalytic activity for 1-hexene under catalytic conditions and has no polar substituent in at least one of $R_1$, $R_2$, $R_3$ and $R_4$ (*Chem. Commun.*, 2002, 858).

However, the prior ligands containing heteroatoms as described above are still required to consistently maintain their polymerization activity during reactions for producing 1-octene or 1-hexene and to have high selectivity.

Further, there is a problem that their activity is greatly reduced when they are supported on a support such as silica (*J. Am. Chem. Soc* 2003, 125, 5272, *Ind. Eng. Chem. Res.* 2008, 47, 5369).

SUMMARY OF THE INVENTION

In order to solve the above problems in the prior art, an object of the present invention is to provide a novel ligand compound having an X—Y—X skeletal structure of which atom is introduced with a terminal functional group.

Further, another object of the present invention is to provide a novel organic chromium compound.

Further, still another object of the present invention is to provide a catalyst system for ethylene oligomerization, which is used to prepare a low-density polyethylene in one reactor by using a small amount of comonomers or by using only ethylene without comonomers, and is able to maintain high catalytic activity and high alpha-olefin selectivity even though supported on a support.

Further, still another object of the present invention is to provide an ethylene oligomerization method using the catalyst system with high polymerization activity and reaction selectivity.

Further, still another object of the present invention is to provide a preparation method of the catalyst system for ethylene oligomerization.

In order to achieve the above objects, the present invention provides a ligand compound represented by the following Chemical Formula 1:

[Chemical Formula 1]

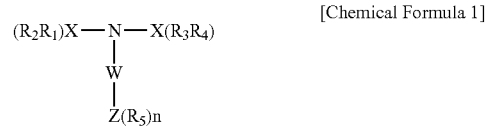

wherein X is phosphorus, arsenic or antimony;

W is a carbon chain having 0 to 10 carbon atoms;

$R_1$, $R_2$, $R_3$ and $R_4$ are each independently hydrocarbyl, substituted hydrocarbyl, heterohydrocarbyl or substituted heterohydrocarbyl;

Z is nitrogen, oxygen or sulfur;

$R_5$ is hydrocarbyl, substituted hydrocarbyl, heterohydrocarbyl or substituted heterohydrocarbyl excluding hydrogen; and n is 1 or 2.

Further, the present invention provides an organic chromium compound represented by the following Chemical Formula 2:

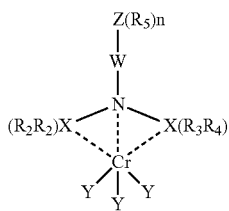

[Chemical Formula 2]

wherein X is phosphorus, arsenic or antimony;

W is a carbon chain having 0 to 10 carbon atoms;

$R_1$, $R_2$, $R_3$ and $R_4$ are each independently hydrocarbyl, substituted hydrocarbyl, heterohydrocarbyl or substituted heterohydrocarbyl;

Z is nitrogen, oxygen or sulfur;

$R_5$ is hydrocarbyl, substituted hydrocarbyl, heterohydrocarbyl or substituted heterohydrocarbyl excluding hydrogen;

Y is each independently halogen, hydrogen, or hydrocarbyl having 1 to 4 carbon atoms; and n is 1 or 2.

Further, the present invention provides a catalyst system for ethylene oligomerization, including the ligand compound represented by Chemical Formula 1 and a chromium source or the organic chromium compound represented by Chemical Formula 2; and a cocatalyst.

Further, the present invention provides an ethylene oligomerization method of polymerizing ethylenes in the presence of the catalyst system for ethylene oligomerization.

Further, the present invention provides a preparation method of the catalyst system for ethylene oligomerization, including the steps of supporting the cocatalyst on a support, and supporting the organic chromium compound represented by Chemical Formula 2 on the cocatalyst-supported support.

Further, the present invention provides a preparation method of the catalyst system for ethylene oligomerization, including the steps of supporting the organic chromium compound represented by Chemical Formula 2 on a support, and supporting the cocatalyst on the organic chromium compound-supported support.

According to the present invention, a low-density polyethylene may be prepared in one reactor by using a small amount of comonomers or by using only ethylene without comonomers.

Further, the catalyst is able to maintain high catalytic activity and alpha-olefin selectivity even though supported on a support, and oligomerization and alpha-olefin preparation can be performed at the same time by a single catalyst, thereby preparing a low-density polyethylene in one reactor by using a small amount of comonomers or by using only ethylene without comonomers.

BRIEF DESCRIPTION OF THE DRAWINGS

FIG. 1 is a photograph showing catalyst systems including respective ligands prepared according to Comparative Preparation Example 1 and Preparation Example 2, which are dissolved in toluene.

DETAILED DESCRIPTION OF THE EMBODIMENTS

The terminology used herein is for the purpose of describing particular embodiments only and is not intended to be limiting of the invention. The singular forms are intended to include the plural forms as well, unless the context clearly indicates otherwise. It will be further understood that the terms "includes, "comprises," or "has" when used in this specification, specify the presence of stated features, integers, steps, components, or combinations thereof, but do not preclude the presence or addition of one or more other features, integers, steps, components, or combinations thereof.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a ligand compound, an organic chromium compound, a catalyst system for ethylene oligomerization, a preparation method thereof, and an ethylene oligomerization method using the same of the present invention will be described in detail.

Ligand Compound

According to an embodiment, the present invention provides a ligand compound represented by the following Chemical Formula 1:

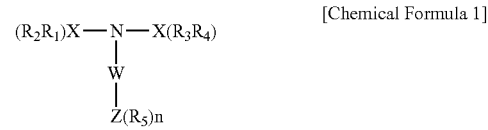

[Chemical Formula 1]

wherein X is phosphorus, arsenic or antimony;

W is a carbon chain having 0 to 10 carbon atoms;

$R_1$, $R_2$, $R_3$ and $R_4$ are each independently hydrocarbyl, substituted hydrocarbyl, heterohydrocarbyl or substituted heterohydrocarbyl;

Z is nitrogen, oxygen or sulfur;

$R_5$ is hydrocarbyl, substituted hydrocarbyl, heterohydrocarbyl or substituted heterohydrocarbyl excluding hydrogen; and n is 1 or 2.

The ligand compound represented by Chemical Formula 1 will be described in more detail. In Chemical Formula 1, X is phosphorus, arsenic or antimony, and preferably phosphorus.

W is a carbon chain having 0 to 10 carbon atoms, and preferably a carbon chain having 0 to 5 carbon atoms.

Z is nitrogen, oxygen or sulfur, and preferably nitrogen.

$R_1$, $R_2$, $R_3$ and $R_4$ are each independently a hydrocarbyl, substituted hydrocarbyl, heterohydrocarbyl or substituted heterohydrocarbyl group, and a non-electron donor. They may be non-polar groups, and suitably, methyl, ethyl, ethylenyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, cumyl, mesityl, biphenyl, naphthyl, anthracenyl, methoxy, ethoxy, phenoxy, tolyloxy, dimethylamino, thiomethyl, trimethylsilyl, dimethylhydrazyl, etc., but are not limited thereto. Preferably, they may be independently selected from cyclohexyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, and o-isopropoxyphenyl.

All of $R_1$, $R_2$, $R_3$ and $R_4$ may be aromatic or substituted aromatic groups.

$R_5$ is a hydrocarbyl, substituted hydrocarbyl, heterohydrocarbyl or substituted heterohydrocarbyl group excluding hydrogen, and specifically, it may be selected from the group consisting of alkyl, aryloxy, halogen, nitro, alkoxycarbonyl, carbonyloxy, alkoxy, aminocarbonyl, carbonylamino, dialkylamino, derivatives thereof and aryl substituted with any substituent.

The ligand compound represented by Chemical Formula 1 may have a PNP-type skeletal structure which is introduced with a novel terminal functional group.

More specifically, according to an embodiment of the present invention, the ligand compound represented by Chemical Formula 1 may be exemplified by one of the following structural formulae, but the present invention is not limited thereto. The following compounds may be prepared by a typical method of preparing a ligand, and a more detailed description thereof will be given in the following Examples.

When the ligand compound is used, a low-density polyethylene may be prepared in one reactor by using a small amount of comonomers or by using only ethylene without comonomers, and in particular, high catalytic activity and high alpha-olefin selectivity may be maintained even though it is supported on a support.

Organic Chromium Compound

According to an embodiment, the present invention provides an organic chromium compound represented by the following Chemical Formula 2:

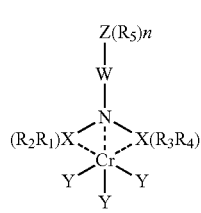

[Chemical Formula 2]

wherein X is phosphorus, arsenic or antimony;

W is a carbon chain having 0 to 10 carbon atoms;

$R_1$, $R_2$, $R_3$ and $R_4$ are each independently hydrocarbyl, substituted hydrocarbyl, heterohydrocarbyl or substituted heterohydrocarbyl;

Z is nitrogen, oxygen or sulfur;

$R_5$ is hydrocarbyl, substituted hydrocarbyl, heterohydrocarbyl or substituted heterohydrocarbyl excluding hydrogen;

Y is each independently halogen, hydrogen, or hydrocarbyl having 1 to 4 carbon atoms; and n is 1 or 2.

Detailed descriptions, specific examples, and preferred examples of n, X, W, Z, $R_1$, $R_2$, $R_3$, $R_4$ and $R_5$ in the organic chromium compound represented by Chemical Formula 2 are the same as in Chemical Formula 1 of the above described ligand compound.

Further, Y may be preferably Cl or a methyl group.

According to an embodiment of the present invention, the organic chromium compound represented by Chemical Formula 2 may be a chromium (Cr) complex of the ligand compound having a PNP-type skeletal structure which is introduced with a novel terminal functional group.

More specifically, the organic chromium compound represented by Chemical Formula 2 may be a Cr complex of the ligand compound represented by one of the following structural formulae, but the present invention is not limited thereto.

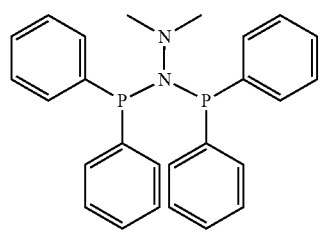

PNP2

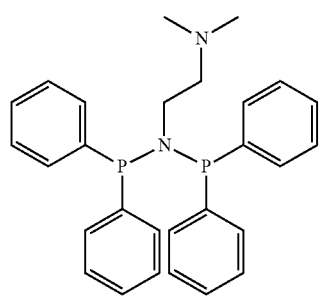

PNP3

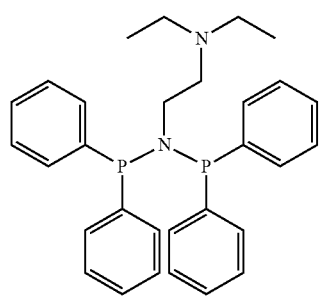

PNP4

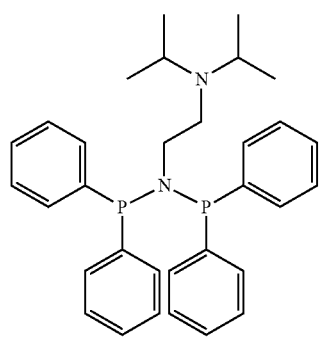

PNP5

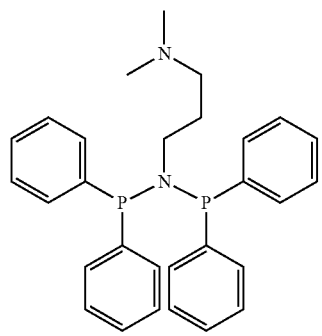

PNP6

The organic chromium compounds may be prepared by a typical method of preparing a transition metal organic compound, and a more detailed description thereof will be given in the following Examples.

When the organic chromium compound is used, a low-density polyethylene may be prepared in one reactor by using a small amount of comonomers or by using only ethylene without comonomers, and in particular, high catalytic activity and high alpha-olefin selectivity may be maintained even though it is supported on a support.

Catalyst System for Ethylene Oligomerization and Ethylene Oligomerization Method Using the Same According to an embodiment of the present invention, the present invention provides a catalyst system for ethylene oligomerization including i) the ligand compound represented by the following Chemical Formula 1 and a chromium source, or ii) the organic chromium compound represented by the following Chemical Formula 2; and a cocatalyst:

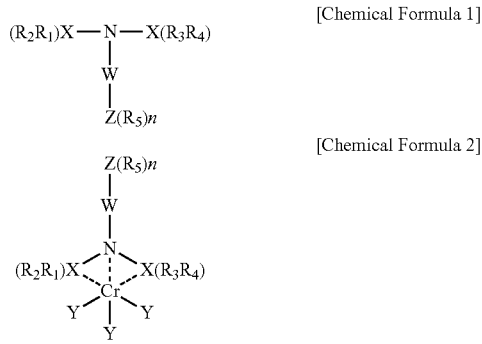

[Chemical Formula 1]

[Chemical Formula 2]

wherein X is phosphorus, arsenic or antimony;

W is a carbon chain having 0 to 10 carbon atoms;

$R_1$, $R_2$, $R_3$ and $R_4$ are each independently hydrocarbyl, substituted hydrocarbyl, heterohydrocarbyl or substituted heterohydrocarbyl;

Z is nitrogen, oxygen or sulfur;

$R_5$ is hydrocarbyl, substituted hydrocarbyl, heterohydrocarbyl or substituted heterohydrocarbyl excluding hydrogen;

Y is each independently halogen, hydrogen, or hydrocarbyl having 1 to 4 carbon atoms; and n is 1 or 2.

As used herein, the term "catalyst system" means an active catalytic composition that can be obtained by adding three components of chromium or a source thereof, the ligand compound and the cocatalyst or alternatively two components of the organic chromium compound and the cocatalyst at the same time, or sequentially in any order in the presence or absence of any proper solvent in the presence or absence of monomers. The three components or two components of the catalyst system may be used without being supported on a support, or if necessary, they may be supported on the support to be used.

Hereinafter, the components of the catalyst system for ethylene oligomerization will be described in more detail.

Detailed descriptions, specific examples, and preferred examples of n, X, W, Y, Z, $R_1$, $R_2$, $R_3$, $R_4$ and $R_5$ in the ligand compound represented by Chemical Formula 1 or the organic chromium compound represented by Chemical Formula 2 that is included in the catalyst system for ethylene oligomerization of the present invention are the same as in the above descriptions of the ligand compound and the organic chromium compound.

In the ligand compound represented by Chemical Formula 1 or the organic chromium compound represented by Chemical Formula 2 that is included in the catalyst system for ethylene oligomerization according to an embodiment of the present invention, a functional group at the ligand having the structure of $(R_1)(R_2)X\text{—}Y\text{—}X(R_3)(R_4)$, namely, $\text{—}W\text{—}Z(R_5)n$ group having a terminal functional group at the N atom is introduced to increase solubility for the catalyst, thereby increasing polymerization activity and selectivity during the polymerization reaction.

According to an embodiment of the present invention, the chromium source may be chromium or a chromium precursor. Specific example of the chromium or chromium precursor may be chromium (III) acetylacetonate, tris(tetrahydrofuran) trichlorochromium, or chromium (III) 2-ethylhexanoate, but the present invention is not limited thereto.

The catalyst system for ethylene oligomerization of the present invention includes a cocatalyst. The cocatalyst may be an organic metal compound containing the Group 13 metal, and the catalyst is not particularly limited, as long as it may be generally used in olefin polymerization in the presence of a catalyst of a transition metal compound.

Specifically, the cocatalyst may be one or more selected from the group consisting of the compounds represented by the following Chemical Formulae 3 to 5, but the present invention is not limited thereto.

—[Al($R^6$)—O]c-     [Chemical Formula 3]

wherein $R^6$ is the same as or different from each other, and each independently a halogen radical, a hydrocarbyl radical having 1 to 20 carbon atoms, a halogen-substituted hydrocarbyl radical having 1 to 20 carbon atoms, and c is an integer of 2 or more, D($R^7$)$_3$     [Chemical Formula 4]

wherein D is aluminium or boron, $R^7$ is hydrocarbyl having 1 to 20 carbon atoms or halogen-substituted hydrocarbyl having 1 to 20 carbon atoms,

[L-H]$^+$[Q(E)$_4$]$^-$     [Chemical Formula 5]

wherein L is a neutral Lewis base, [L-H]$^+$ is a Bronsted acid, Q is boron or aluminium in the +3 oxidation state, E is each independently an aryl group having 6 to 20 carbon atoms or an alkyl group having 1 to 20 carbon atoms in which one or more hydrogen atoms are substituted or unsubstituted with halogen, hydrocarbyl having 1 to 20 carbon atoms, an alkoxy functional group or a phenoxy functional group.

Examples of the compound represented by Chemical Formula 3 may include methylaluminoxane (MAO), ethyl aluminoxane, isobutyl aluminoxane, butyl aluminoxane or the like.

Examples of the alkyl metal compound represented by Chemical Formula 4 may include trimethylaluminium, triethylaluminium, triisobutylaluminium, tripropylaluminium, tributylaluminium, dimethylchloroaluminium, dimethylisobutylaluminium, dimethylethylaluminium, diethylchloroaluminium, triisopropylaluminium, tri-s-butylaluminium, tricyclopentylaluminium, tripentylaluminium, triisopentylaluminium, trihexylaluminium, ethyldimethylaluminium, methyldiethylaluminium, triphenylaluminium, tri-p-tolylaluminium, dimethylaluminiummethoxide, dimethylaluminiumethoxide, trimethylboron, triethylboron, triisobutylboron, tripropylboron, tributylboron or the like.

Examples of the compound represented by Chemical Formula 5 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenyl boron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminium, tributylammoniumtetraphenylaluminium, trimethylammoniumtetraphenylaluminium, tripropylammoniumtetraphenylaluminium, trimethylammoniumtetra(p-tolyl)aluminium, tripropylammoniumtetra(p-tolyl)aluminium, triethylammoniumtetra(o,p-dimethylphenyl)aluminium, tributylammoniumtetra(p-trifluoromethylphenyl)aluminium, trimethylammoniumtetra(p-trifluoromethylphenyl)aluminium, tributylammoniumtetrapentafluorophenylaluminium, N,N-diethylaniliniumtetraphenylaluminium, N,N-diethylaniliniumtetraphenylaluminium, N,N-diethylaniliniumtetrapentafluorophenylaluminium, diethylammoniumtetrapentafluorophenylaluminium, triphenylphosphoniumtetraphenylaluminium, trimethylphosphoniumtetraphenylaluminium, triphenylcarboniumtetraphenylboron, triphenylcarboniumtetraphenylaluminium, triphenylcarboniumtetra(p-trifluoromethylphenyl)boron, triphenylcarboniumtetrapentafluorophenylboron, or the like.

It may be preferably, alumoxane, and more preferably, methyl alumoxane (MAO) which is alkyl alumoxane.

According to an embodiment of the present invention, the catalyst system for ethylene oligomerization may include the ligand compound represented by Chemical Formula 1, the chromium source and the cocatalyst. In this regard, a molar ratio of ligand compound:chromium source:cocatalyst may be about 1:1:1 to about 10:1:10,000, and preferably, about 1:1:100 to about 5:1:3,000, in order to increase selectivity for linear alpha-olefin and polymerization activity. However, the present invention is not limited thereto.

The catalyst system including the ligand compound represented by Chemical Formula 1, the chromium source and the cocatalyst may be obtained as an active catalyst by adding three components of the catalyst system at the same time, or sequentially in any order in the presence or absence of monomers in any proper solvent. The proper solvent may include heptane, toluene, 1-hexene, diethyl ether, tetrahydrofuran, acetonitrile, dichloromethane, chloroform, chlorobenzene, methanol, acetone or the like, but is not limited thereto.

According to another embodiment of the present invention, the catalyst system for ethylene oligomerization may include the organic chromium compound represented by Chemical Formula 2 and the cocatalyst.

Further, the catalyst system including the organic chromium compound represented by Chemical Formula 2 and the cocatalyst may further include a support, and it may be supported on the support.

Many known organic chromium catalysts include methyl aluminoxane (hereinafter, referred to as "MAO") or borate as a cocatalyst to prepare 1-hexene with high activity and selectivity in a solution reaction. However, theses catalysts show the property that when they are used as supported catalysts prepared by supporting them on supports, together with the cocatalyst, their activity is greatly reduced.

However, when the catalyst system for ethylene oligomerization according to the present invention is used to prepare polyolefin, it may exhibit high selectivity for comonomers such as 1-hexene or 1-octene, which are injected for low-density polyethylene polymerization. Therefore, low-density polyethylene polymerization is possible in one reactor without injection of additional comonomers.

Further, upon preparation of such catalyst, it may exhibit high activity irrespective of the supporting order of the cocatalyst and the organic chromium compound. That is, when the catalyst is prepared by supporting the organic chromium compound, or the ligand compound and the chromium source on the support and then supporting the cocatalyst thereto as well as when the catalyst is prepared by supporting the cocatalyst on the support, and then supporting the cocatalyst thereto by the ordinary method, the catalyst may exhibit high selectivity for comonomers such as 1-hexene or 1-octene without reduction in the catalytic activity during polyolefin polymerization.

In the catalyst system for ethylene oligomerization of the present invention, when the above described organic chromium compound and cocatalyst are supported on the support, there are no limitations in constitution of the respective component contents. However, in order to increase selectivity for linear alpha-olefin and olefin polymerization efficiency, a molar ratio of organic chromium compound:cocatalyst may be about 1:5 to about 1:1,000, and preferably, about 1:10 to about 1:250, but is not limited thereto.

Further, the organic chromium compound and the cocatalyst may be included in an amount of about 0.5 to about 20 parts by weight, and about 1 to about 1,000 parts by weight, based on 100 parts by weight of the support, respectively.

Preferably, the organic chromium compound and the cocatalyst may be included in an amount of about 1 to about 15 parts by weight, and about 10 to about 500 parts by weight, based on 100 parts by weight of the support, respectively. Most preferably, the organic chromium compound and the cocatalyst may be included in an amount of about 1 to about 100 parts by weight, and about 40 to about 150 parts by weight, respectively.

Meanwhile, as long as the support is metal, metal salt, or metal oxide which is used in the typical supported catalysts, there is no limitation in the constitution. Specifically, any one support selected from the group consisting of silica, silica-alumina and silica-magnesia may be included. The support may be dried at a high temperature, and typically include a metal oxide, carbonate, sulfate, or nitrate, such as $Na_2O$, $K_2CO_3$, $BaSO_4$ and $Mg(NO_3)_2$.

It is preferable that the number of surface hydroxyl groups (—OH) of the support is as small as possible. Practically, it is difficult to remove all of the hydroxyl groups. The number of hydroxyl groups may be controlled by the support preparation method and conditions, and drying conditions (temperature, time, drying method, etc.), and it may be preferably about 0.1 to about 10 mmol/g, more preferably about 0.1 to about 1 mmol/g, and much more preferably about 0.1 to about 0.5 mmol/g. In order to prevent side reaction due to the trace hydroxyl group remaining after drying, it is possible to use a support of which hydroxyl groups are removed chemically while preserving the highly reactive siloxane groups participating in supporting.

According to another embodiment, the present invention provides an ethylene oligomerization method of polymerizing ethylene in the presence of the catalyst system for ethylene oligomerization.

In the ethylene oligomerization method of the present invention, detailed descriptions, specific examples, and preferred examples of n, X, W, Y, Z, $R_1$, $R_2$, $R_3$, $R_4$ and $R_5$ in the ligand compound represented by Chemical Formula 1 or the organic chromium compound represented by Chemical Formula 2 are the same as in the above described ligand compound and organic chromium compound. Further, detailed descriptions, specific examples, and preferred examples of the chromium source and the cocatalyst are the same as in the above described catalyst system for ethylene oligomerization.

The ethylene oligomerization may be prepared through a homogeneous liquid reaction, which is conducted in the presence or absence of an inactive solvent using the above described catalyst system according to embodiment, general apparatuses and a conventional contact technology, a slurry reaction, in which a part of the catalyst system or all of the catalyst system is not dissolved, a two-phase liquid-liquid reaction, or a bulk phase or gas phase reaction in which the product olefin acts as a main medium.

The ethylene oligomerization may be performed in the presence of the catalyst compound and an arbitrary inactive solvent that does not react with an active agent. The proper inactive solvents may include, but are not limited to, benzene, toluene, xylene, cumene, heptane, cyclohexane, methylcyclohexane, methylcyclopentane, n-hexane, 1-hexene, 1-octene or the like.

According to an embodiment, the ethylene oligomerization reaction may be conducted at a temperature of about 0 to about 150° C., preferably about 40 to about 100° C., more preferably about 50 to about 90° C. and at a pressure of about 15 to about 1500 psig, and preferably about 15 to about 700 psig.

1-hexene or 1-octene may be produced with high activity and high selectivity by ethylene oligomerization using the above described catalyst system according to an embodiment. Therefore, a low-density polyethylene may be prepared in one reactor by using a small amount of comonomers or by using only ethylene without comonomers.

Preparation Method of Catalyst System for Ethylene Oligomerization

The present invention provides a preparation method of the catalyst system for ethylene oligomerization.

Specifically, the preparation method of the catalyst system for ethylene oligomerization according to an embodiment of the present invention includes the steps of supporting the cocatalyst on a support, and supporting the organic chromium compound represented by the following Chemical Formula 2 on the cocatalyst-supported support:

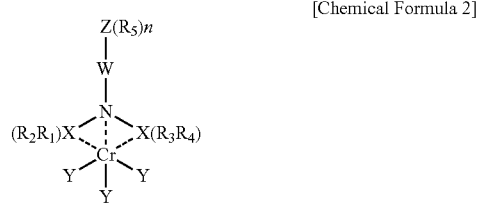

[Chemical Formula 2]

wherein X is phosphorus, arsenic or antimony;
W is a carbon chain having 0 to 10 carbon atoms;
$R_1$, $R_2$, $R_3$ and $R_4$ are each independently hydrocarbyl, substituted hydrocarbyl, heterohydrocarbyl or substituted heterohydrocarbyl;
Z is nitrogen, oxygen or sulfur;

$R_5$ is hydrocarbyl, substituted hydrocarbyl, heterohydrocarbyl or substituted heterohydrocarbyl excluding hydrogen;
Y is each independently halogen, hydrogen, or hydrocarbyl having 1 to 4 carbon atoms; and
n is 1 or 2.

Further, the preparation method of the catalyst system for ethylene oligomerization according to another embodiment of the present invention includes the steps of supporting the organic chromium compound represented by Chemical Formula 2 on a support, and supporting the cocatalyst on the organic chromium compound-supported support.

Meanwhile, in the preparation method of the catalyst system for ethylene oligomerization according to an embodiment of the present invention, detailed descriptions, specific examples, and preferred examples of Chemical Formula 2 and the cocatalyst are the same as in the above described catalyst system for ethylene oligomerization.

In the preparation method of the catalyst system for ethylene oligomerization according to an embodiment of the present invention, the catalyst system for ethylene oligomerization may be prepared by supporting the cocatalyst on the support, and then supporting the organic chromium compound represented by Chemical Formula 2 on the cocatalyst-supported support.

Alternatively, in the preparation method of the catalyst system for ethylene oligomerization according to another embodiment of the present invention, the catalyst system for ethylene oligomerization may be prepared by supporting the organic chromium compound represented by Chemical Formula 2 on the support, and then supporting the cocatalyst thereto.

That is, even though the catalyst is prepared by changing the supporting order of the organic chromium compound and the cocatalyst, it may maintain its catalytic activity and exhibit high selectivity for linear alpha-olefin and high catalytic activity.

Therefore, unlike the typical preparation method of the catalyst system for ethylene oligomerization, the cocatalyst may be supported on the support after supporting the organic chromium compound, and thus it is possible to easily control the supporting amount of the organic chromium compound. Accordingly, in order to increase selectivity for linear alpha-olefin such as 1-hexene or 1-octene, the supporting amount of the organic chromium compound may be controlled, thereby polymerizing olefins having various physical properties, such as low-density polyethylene (PE).

As mentioned above, since the catalyst system for ethylene oligomerization according to the above embodiments and/or the catalyst system prepared by the preparation method of the catalyst system for ethylene oligomerization according to the above embodiments include(s) the organic chromium compound showing high selectivity for linear alpha-olefin, olefins having various physical properties may be polymerized using a single catalyst.

In particular, when polyolefins such low-density polyethylene are prepared using the catalyst including the organic chromium compound with high selectivity for linear alpha-olefin such as 1-hexene and/or 1-octene, no additional injection of linear alpha-olefin such as 1-hexene and/or 1-octene is required, resulting in economical production process. Further, even though the supporting order of the organic chromium compound and the cocatalyst is changed, the catalyst maintains its catalytic activity, and exhibits high selectivity for linear alpha-olefin and high catalytic activity. Thus, it is possible to easily control the supporting amount of the organic chromium compound.

Hereinafter, actions and effects of the present invention will be explained in further detail with reference to the specific examples of the present invention. However, it should be understood that these examples are merely illustrative of the present invention and the scope of the present invention is not to be determined by them.

EXAMPLE

Synthesis of Ligand

Preparation Example 1

PNP2: Synthesis of $(C_6H_5)_2PN(NMe_2)P(C_6H_5)_2$

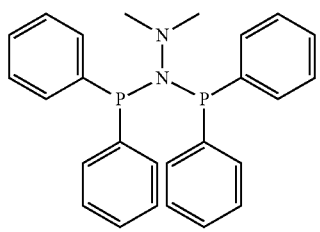

PNP2

1,1-dimethylhydrazine HCl (1.10 g, 13.5 mmol) and 18.75 mL of triethylamine were added to a flask containing 62.5 mL of dichloromethane. Chlorodiphenylphosphine (2.5 mL, 13.5 mmol) was added thereto, followed by agitation for 30 minutes. Chlorodiphenylphosphine (2.5 mL, 13.5 mmol) was further added, followed by agitation overnight. A trimethylammonium salt was filtered and the solvent was removed to obtain a white solid. A clear crystal was finally obtained by recrystallization from methanol/dichloromethane.

$^1$H NMR(CDCl$_3$): δ 2.50 (6H, s, N(CH$_3$)$_2$), 7.24-7.47 (20H, m, ArH)

$^{13}$C NMR(CDCl$_3$): δ 7.48, 47.55, 47.62 (N(CH$_3$)$_2$), 128.87, 127.93, 128.68, 133.19, 133.41, 139.56, 139.70 (ArC)

Preparation Example 2

PNP3: Synthesis of $(C_6H_5)_2PN(CH_2CH_2NMe_2)P(C_6H_5)_2$

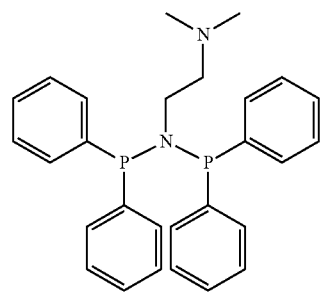

PNP3

N,N-dimethylethylenediamine (1.47 mL, 13.5 mmol) and 18.75 mL of triethylamine were added to a flask containing 62.5 mL of dichloromethane. Chlorodiphenylphosphine (2.5 mL, 13.5 mmol) was added thereto, followed by agitation for 30 minutes. Chlorodiphenylphosphine (2.5 mL, 13.5 mmol) was further added, followed by agitation overnight. A trimethylammonium salt was filtered and the solvent was removed. The resultant was separated by column chromatography (silica gel, ethyl acetate). A highly sticky liquid was finally obtained.

$^1$H NMR(CDCl$_3$): δ 1.96 (8H, m, CH$_2$N(CH$_3$)$_2$), 7.24-7.47 (20H, m, ArH)

$^{13}$C NMR(CDCl$_3$): δ 46.58 (N(CH$_3$)$_2$), 50.682 (NCH$_2$), 59.51 (CH$_2$NMe$_2$), 128.03, 128.06, 128.09, 128.75, 132.59, 132.70, 132.81, 139.33, 139.39, 139.45 (ArC)

$^{31}$P NMR(CDCl$_3$): δ 63.7(s)

Preparation Example 3

PNP4: Synthesis of $(C_6H_5)_2PN(CH_2CH_2NEt_2)P(C_6H_5)_2$

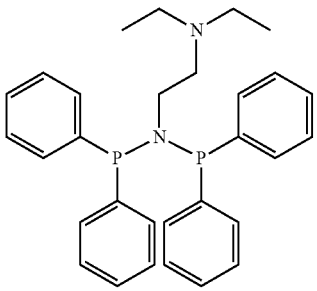

PNP4

N,N-diethylethylenediamine (1.91 mL, 13.5 mmol) and 18.75 mL of triethylamine were added to a flask containing 62.5 mL of dichloromethane. Chlorodiphenylphosphine (2.5 mL, 13.5 mmol) was added thereto, followed by agitation for 30 minutes. Chlorodiphenylphosphine (2.5 mL, 13.5 mmol) was further added, followed by agitation overnight. A trimethylammonium salt was filtered and the solvent was removed. The resultant was dissolved in diethylether and passed through alumina. After drying, a highly sticky liquid was separated.

$^1$H NMR(CDCl$_3$): δ 0.78 (6H, t, N(CH$_2$CH$_3$)$_2$), 2.12 (2H, t, NCH$_2$CH$_2$NEt$_2$), 2.25 (4H, q, N(CH$_2$CH$_3$)$_2$), 3.42 (2H, m, N(CH$_2$), 7.24-7.42 (20H, m, ArH)

$^{13}$C NMR(CDCl$_3$): δ11.88 (N(CH$_2$CH$_3$)$_2$), 47.34 (N(CH$_2$CH$_3$)$_2$), 50.91 (NCH$_2$), 53.33 (CH$_2$NMe$_2$), 128.01, 128.04, 128.07, 128.69, 132.59, 132.70, 132.81, 139.41, 139.54 (ArC)

$^{31}$P NMR(CDCl$_3$): δ 63.1(s)

Preparation Example 4

PNP4: Synthesis of $(C_6H_5)_2PN(CH_2CH_2NPr_2)P(C_6H_5)_2$

PNP5

N,N-diisopropylethylenediamine (2.24 mL, 12.9 mmol) and 18.75 mL of triethylamine were added to a flask containing 62.5 mL of dichloromethane. Chlorodiphenylphosphine (2.5 mL, 13.5 mmol) was added thereto, followed by agitation for 30 minutes. Chlorodiphenylphosphine (2.5 mL, 13.5 mmol) was further added, followed by agitation overnight. A trimethylammonium salt was filtered and the solvent was removed. The resultant was dissolved in diethylether and passed through alumina, followed by column chromatography (silica gel, ethyl acetate). Thus, a ligand was obtained as a highly sticky liquid.

$^1$H NMR(CDCl$_3$): δ 0.74 (12H, d, N(CH$_2$CH$_3$)$_2$), 2.18 (2H, t, CH$_2$NiPr$_2$), 2.25 (4H, sept, N(CH(CH$_3$)$_2$)$_2$), 3.30 (2H, m, NCH$_2$), 7.24-7.42 (20H, m, ArH)

$^{13}$C NMR(CDCl$_3$): δ 20.79 (N(CH(CH$_3$)$_2$)$_2$), 46.25 (NCH$_2$), 48.80 (N(CH(CH$_3$)$_2$)$_2$), 54.12 (CH$_2$NiPr$_2$), 127.99, 128.02, 128.05, 128.69, 132.59, 132.70, 132.81, 139.41, 139.54 (ArC)

$^{31}$P NMR(CDCl$_3$): δ 61.9(s)

Preparation Example 5

PNP6: Synthesis of (C$_6$H$_5$)$_2$PN(CH$_2$CH$_2$CH$_2$NMe$_2$)P(C$_6$H$_5$)$_2$

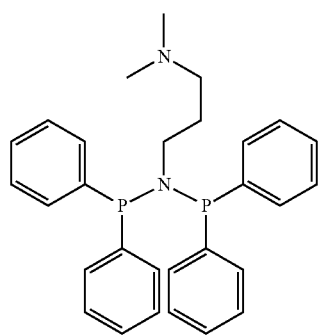

PNP6

N,N-dimethyl-1,3-propanediamine (0.65 mL, 5.15 mmol) and 7.5 mL of triethylamine were added to a flask containing 30 mL of dichloromethane. Chlorodiphenylphosphine (1 mL, 5.4 mmol) was added thereto, followed by agitation for 30 minutes. Chlorodiphenylphosphine (1 mL, 5.4 mmol) was further added, followed by agitation overnight. A trimethylammonium salt was filtered and the solvent was removed. The resultant was subjected to column chromatography (silica gel, ethyl acetate) to obtain a ligand as a highly sticky liquid.

$^1$H NMR(CDCl$_3$): δ 1.26 (12H, quin, NCH$_2$CH$_2$CH$_2$NMe$_2$), 1.82 (2H, t, CH$_2$NMe$_2$), 1.84 (6H, s, N(CH$_3$)$_2$), 3.29 (2H, m, NCH$_2$), 7.21-7.39 (20H, m, ArH)

$^{13}$C NMR(CDCl$_3$): δ 29.26 (NCH$_2$CH$_2$CH$_2$NMe$_2$), 45.26 (N(CH$_3$)$_2$), 51.12 (NCH$_2$), 57.15 (CH$_2$NMe$_2$), 128.01, 128.04, 128.70, 132.60, 132.71, 132.82, 139.46, 139.52, 139.58 (ArC)

$^{31}$P NMR(CDCl$_3$): δ 63.0 (s)

Comparative Preparation Example 1

PNP4: Synthesis of (C$_6$H$_5$)$_2$PNPrP(C$_6$H$_5$)$_2$

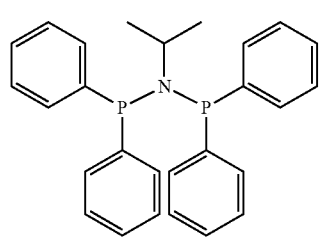

PNP1

Isopropylamine (1.16 g, 13.5 mmol) and 18.75 mL of triethylamine were added to a flask containing 62.5 mL of dichloromethane. Chlorodiphenylphosphine (2.5 mL, 13.5 mmol) was added thereto, followed by agitation for 30 minutes. Chlorodiphenylphosphine (2.5 mL, 13.5 mmol) was further added, followed by agitation overnight. A trimethylammonium salt was filtered and the solvent was removed to obtain a white solid. A clear crystal was finally obtained as a ligand by recrystallization from methanol/dichloromethane.

The catalyst systems including respective ligands prepared in Preparation Example 2 and Comparative Preparation Example 1, which were dissolved in toluene as a solvent used for ethylene oligomerization, are compared in the photograph of FIG. 1.

Referring to FIG. 1, the prior PNP-type catalyst system according to Comparative Preparation Example 1 was not dissolved and thus was dispersed as aggregates (left), whereas PNP3 of the present invention according to Preparation Example 2 was uniformly dissolved (right).

Synthesis of Organic Chromium Compound

Preparation Example 6

0.2 mmol of CrCl$_3$(THF)$_3$ and 10 ml of pure THF were added to a Schlenk flask under an argon atmosphere. 0.2 mmol of the PNP2 ligand prepared in Preparation Example 1 in 10 ml of pure THF solution was also added to a Schlenk flask under an argon atmosphere. Each solution was cooled to −5° C. and the ligand solution was slowly added via cannula to a CrCl$_3$(THF)$_3$ solution. The color of the solution slowly changed from purple to green, and the temperature was slowly raised to room temperature, followed by agitation overnight. The solvent of the reaction mixture was removed under reduced pressure, and the resulting sticky dark green solid was dissolved in 50 ml of pure toluene so as to prepare a CrCl$_3$ complex of PNP2.

Preparation Example 7

A CrCl$_3$ complex of PNP3 was prepared in the same manner as in Preparation Example 6, except that 0.2 mmol of the PNP3 ligand prepared in Preparation Example 2 was used.

Preparation Example 8

A CrCl$_3$ complex of PNP4 was prepared in the same manner as in Preparation Example 6, except that 0.2 mmol of the PNP4 ligand prepared in Preparation Example 3 was used.

Preparation Example 9

A $CrCl_3$ complex of PNP5 was prepared in the same manner as in Preparation Example 6, except that 0.2 mmol of the PNP5 ligand prepared in Preparation Example 4 was used.

Preparation Example 10

A $CrCl_3$ complex of PNP6 was prepared in the same manner as in Preparation Example 6, except that 0.2 mmol of the PNP6 ligand prepared in Preparation Example 5 was used.

Ethylene Oligomerization with Catalyst System

Example 1

Andrew glass was assembled and heated with a torch under vacuum, and then cooled. Toluene (230 ml) and MAO were injected sequentially under nitrogen. Thereafter, 20 mg of the PNP3 ligand which was separately prepared in Preparation Example 2 and 20 μmol of chromium source solution (10 mmol slurry in toluene, 2 mL) were injected. In this regard, a molar ratio of Al/Cr was allowed to be 600 (10% MAO solution in toluene, 10 mL).

The solution was agitated at an agitation speed of 600 rpm under a 50 psig pressure of ethylene. After reaction at 90° C. for 1 hour, the supply of ethylene was stopped, and cooled in iced water. The excessive ethylene was discharged from the reactor, and 1 mL of nonane was added as an internal standard. A small amount of the sample was taken and water was added thereto to separate an organic layer. Anhydrous magnesium sulfate was added to remove water and the composition was analyzed by GC. Methanol was added to the rest of the organic layer and then filtered to obtain a solid product. This solid product was dried in an oven overnight and then weighed.

If the activity is intended to be determined by the weight, the weight before the supply of ethylene is measured and the weight after the discharge of ethylene after reaction was measured, and a difference therebetween was converted into the activity. In this case, without addition of the internal standard, the composition was analyzed by GC.

Example 2

Experiment was performed in the same manner as in Example 1, except that 20 mg of PNP2 of Preparation Example 1 was used as the ligand.

Example 3

Experiment was performed in the same manner as in Example 1, except that 25 mg of PNP6 of Preparation Example 5 was used as the ligand.

Example 4

Experiment was performed in the same manner as in Example 1, except that reaction was carried out at 60° C. for 1 hour.

Example 5

Experiment was performed in the same manner as in Example 4, except that 20 mg of PNP2 of Preparation Example 1 was used as the ligand.

Example 6

Experiment was performed in the same manner as in Example 4, except that 25 mg of PNP6 of Preparation Example 5 was used as the ligand.

Comparative Example 1

Experiment was performed in the same manner as in Example 1, except that 20 mg of PNP1 of Comparative Preparation Example 1 was used as the ligand.

Comparative Example 2

Experiment was performed in the same manner as in Example 4, except that 20 mg of PNP1 of Comparative Preparation Example 1 was used as the ligand.

Results of Examples 1 to 6 and Comparative Examples 1 and 2 are given in the following Table 1.

TABLE 1

| | Ligand | Polymerization temperature (unit: ° C.) | Activity (g/mol · Cr/hr) | Polyethylene (wt %) | GC Area (unit: %) | | | |
|---|---|---|---|---|---|---|---|---|
| | | | | | 1-Bu | 1-Hx | 1-Oc | 1-De |
| Example 1 | PNP3 | 90 | 520,000 | 0.60 | 3.3 | 24.5 | 55.9 | 1.4 |
| Example 2 | PNP2 | 90 | 335,000 | 0.70 | 3.1 | 23.7 | 55.6 | 1.2 |
| Example 3 | PNP6 | 90 | 610,000 | 0.65 | 2.4 | 27.1 | 50.7 | 1.9 |
| Example 4 | PNP3 | 60 | 463,000 | 0.90 | 4.7 | 25.9 | 59.8 | 1.8 |
| Example 5 | PNP2 | 60 | 335,000 | 1.05 | 5.6 | 26.3 | 53.3 | 1.5 |
| Example 6 | PNP6 | 60 | 880,000 | 1.34 | 3.1 | 30.8 | 55.9 | 2.5 |
| Comparative Example 1 | PNP1 | 90 | 198,000 | 0.86 | 16.4 | 7.7 | 8.5 | 12.6 |
| Comparative Example 2 | PNP1 | 60 | 198,000 | 2.91 | 10.8 | 9.4 | 13.3 | 15.1 |

According to the results of Table 1, Examples 1 to 6 showed very high polymerization activity and remarkably enhanced selectivity for 1-hexene and 1-octene, compared to Comparative Examples 1 and 2.

Preparation of Supported Catalyst

Example 7

1.0 g of silica (manufactured by Grace Davison, XP02410) was put in a glass reactor, and 10 ml of toluene was added thereto. 5 mL of 10 wt % methylalumoxane (MAO)/toluene solution was added and allowed to react slowly at 60° C. under agitation. Thereafter, the unreacted aluminium compound was removed by washing with a sufficient amount of toluene. Then, the remaining toluene was removed under reduced pressure at 80° C. 10 mL of toluene was further added, and then 30 mg of the PNP3-CrCl$_3$ complex catalyst prepared in Preparation Example 7 in toluene was added thereto, and allowed to react for 1 hour. After reaction, agitation was stopped and the toluene layer was separated and removed, followed by washing with 20 mL of toluene once. Thereafter, the solution was removed by filtration. The resultant was washed with toluene twice and dried under reduced pressure to give a solid powder.

Example 8

A supported catalyst was prepared in the same manner as in Example 7, except that 60 mg of the PNP3-CrCl$_3$ complex catalyst was used.

Example 9

1.0 g of silica (manufactured by Grace Davison, XP02410) was put in a glass reactor, and 10 ml of toluene was added thereto. 60 mg of the PNP3-CrCl$_3$ complex catalyst prepared in Preparation Example 7 in toluene was added thereto, and allowed to react for 1 hour. After reaction, agitation was stopped and the toluene layer was separated and removed, followed by washing with 20 mL of toluene once. 5 mL of 10 wt % methylalumoxane(MAO)/toluene solution was added thereto, and allowed to react slowly at 60° C. under agitation. Thereafter, the unreacted aluminium compound was removed by washing with a sufficient amount of toluene. Then, the remaining toluene was removed under reduced pressure at 80° C., and the solution was removed by filtration. The resultant was washed with toluene twice and dried under reduced pressure to give a solid powder.

Example 10

A supported catalyst was prepared in the same manner as in Example 8, except that 60 mg of the PNP2-CrCl$_3$ complex catalyst prepared in Preparation Example 6 was used.

Example 11

A supported catalyst was prepared in the same manner as in Example 8, except that 60 mg of the PNP6-CrCl$_3$ complex catalyst prepared in Preparation Example 10 was used.

With regard to the supported catalysts of Examples 7 to 11, the supporting order and the supporting amount of the catalyst are given in the following Table 2.

TABLE 2

| No. | Supporting order | Supporting amount of catalyst (unit: wt %) |
|---|---|---|
| Example 7 | S/M/PNP3 | 3 |
| Example 8 | S/M/PNP3 | 6 |
| Example 9 | S/PNP3/M | 6 |
| Example 10 | S/M/PNP2 | 6 |
| Example 11 | S/M/PNP6 | 6 |

In Table 2, S represents silica, M represents MAO, and PNP3, PNP2, and PNP6 represent the ligand compound structures included in the respective organic chromium compounds.

Ethylene Oligomerization with Supported Catalyst

Example 12

50 mg of the supported catalyst prepared in Example 7 was weighed in a dry box and put in a 50 mL glass bottle. The bottle was sealed with a rubber diaphragm and taken out of the dry box, and a catalyst was ready for injection. The polymerization was performed in a 2 L temperature-controllable metal alloy reactor for high pressure, equipped with a mechanical stirrer.

1 L of hexane containing 1.0 mmol of triethylaluminium and 1-hexene (20 mL) were added to the reactor, and then the prepared supported catalyst was added thereto without contact with air. Polymerization was carried out for 1 hour at 90° C., continuously applying a gaseous ethylene monomer at a pressure of 40 bar. The polymerization was terminated by stopping the agitation and then by exhausting ethylene.

The resulting polymer was filtered through a polymerization solvent and dried in an 80° C. vacuum oven for 4 hours.

Example 13

Polymerization was carried out in the same manner as in Example 12, except that the supported catalyst prepared in Example 8 was used.

Example 14

Polymerization was carried out in the same manner as in Example 12, except that the supported catalyst prepared in Example 9 was used.

Example 15

Polymerization was carried out in the same manner as in Example 12, except that the supported catalyst prepared in Example 9 was used and the polymerization temperature was 60° C.

Example 16

Polymerization was carried out in the same manner as in Example 12, except that the supported catalyst prepared in Example 9 was used and the polymerization pressure was 10 bar.

Example 17

Polymerization was carried out in the same manner as in Example 12, except that the supported catalyst prepared in Example 10 was used.

Example 18

Polymerization was carried out in the same manner as in Example 12, except that the supported catalyst prepared in Example 11 was used.

Polymerization activity and selectivity for 1-hexene/1-octene of Examples 12 to 18 are given in the following Table 3.

TABLE 3

| No. | Supported catalyst | Polymerization temperature (unit: °C.) | Polymerization pressure (unit: bar) | Selectivity 1-Hexene (unit: %) | Selectivity 1Octene (unit: %) | Activity (unit: g/g Cr/hr) |
|---|---|---|---|---|---|---|
| Example 12 | Example 7 | 90 | 40 | 33.7 | 65.3 | 5,562 |
| Example 13 | Example 8 | 90 | 40 | 34.2 | 64.9 | 8,442 |
| Example 14 | Example 9 | 90 | 40 | 35.2 | 63.9 | 7,150 |
| Example 15 | Example 9 | 60 | 40 | 41.0 | 57.9 | 5,212 |
| Example 16 | Example 9 | 90 | 10 | 35.3 | 63.2 | 3,021 |
| Example 17 | Example 10 | 90 | 40 | 36.9 | 61.6 | 3,953 |
| Example 18 | Example 11 | 90 | 40 | 28.0 | 71.3 | 10,868 |

Referring to Table 3, the catalyst system for ethylene oligomerization according to the present invention is used to prepare a low-density polyethylene in one reactor by using a small amount of comonomers or by using only ethylene without comonomers while maintaining high catalytic activity and high alpha-olefin selectivity, even though supported on a support.

What is claimed is:

1. A ligand compound represented by the following Chemical Formula 1:

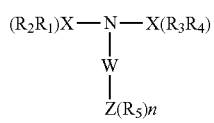

[Chemical Formula 1]

wherein X is phosphorus, arsenic or antimony;
W is ethylene or propylene;
$R_1$, $R_2$, $R_3$ and $R_4$ are each independently hydrocarbyl;
Z is nitrogen;
$R_5$ is hydrocarbyl; and
n is 2.

2. The ligand compound of claim 1, wherein the ligand compound represented by Chemical Formula 1 is selected from the group consisting of $(C_6H_5)_2PN(CH_2CH_2NMe_2)P(C_6H_5)_2$, $(C_6H_5)_2PN(CH_2CH_2NEt_2)P(C_6H_5)_2$, $(C_6H_5)_2PN(CH_2CH_2NPr_2)P(C_6H_5)_2$, and $(C_6H_5)_2PN(CH_2CH_2CH_2NMe_2)P(C_6H_5)_2$.

3. An organic chromium compound represented by the following Chemical Formula 2:

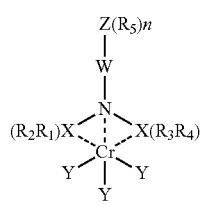

[Chemical Formula 2]

wherein X is phosphorus, arsenic or antimony;
W is ethylene or propylene;
$R_1$, $R_2$, $R_3$ and $R_4$ are each independently hydrocarbyl;
Z is nitrogen;
$R_5$ is hydrocarbyl;
Y is each independently halogen, hydrogen, or hydrocarbyl having 1 to 4 carbon atoms; and
n is 2.

4. The organic chromium compound of claim 3, wherein Y is Cl or methyl.

5. A catalyst system for ethylene oligomerization, comprising i) a ligand compound represented by the following Chemical Formula 1 and a chromium source, or ii) an organic chromium compound represented by the following Chemical Formula 2; and a cocatalyst:

[Chemical Formula 1]

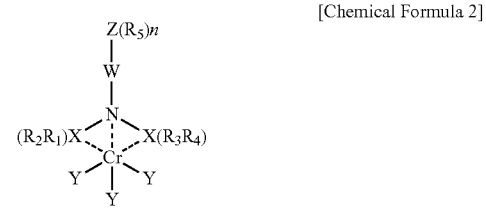

[Chemical Formula 2]

wherein X is phosphorus, arsenic or antimony;
W is ethylene or propylene;
$R_1$, $R_2$, $R_3$ and $R_4$ are each independently hydrocarbyl;
Z is nitrogen;
$R_5$ is hydrocarbyl;
Y is each independently halogen, hydrogen, or hydrocarbyl having 1 to 4 carbon atoms; and
n is 2.

6. The catalyst system for ethylene oligomerization of claim 5, wherein the ligand compound represented by Chemical Formula 1 is selected from the group consisting of $(C_6H_5)_2PN(CH_2CH_2NMe_2)P(C_6H_5)_2$, $(C_6H_5)_2PN(CH_2CH_2NEt_2)P(C_6H_5)_2$, $(C_6H_5)_2PN(CH_2CH_2NPr_2)P(C_6H_5)_2$ and $(C_6H_5)_2PN(CH_2CH_2CH_2NMe_2)P(C_6H_5)_2$.

7. The catalyst system for ethylene oligomerization of claim 5, wherein in Chemical Formula 2, Y is Cl or methyl.

8. The catalyst system for ethylene oligomerization of claim 5, wherein the chromium source is selected from the group consisting of chromium (III) acetylacetonate, tris(tetrahydrofuran) trichlorochromium, and chromium (III) 2-ethylhexanoate.

9. The catalyst system for ethylene oligomerization of claim 5, wherein the cocatalyst is one or more selected from the group consisting of the compounds represented by the following Chemical Formulae 3 to 5:

—[Al(R$^6$)—O]$_c$-  [Chemical Formula 3]

wherein R$^6$ is the same as or different from each other, and each independently a halogen radical, a hydrocarbyl radical having 1 to 20 carbon atoms, a halogen-substituted hydrocarbyl radical having 1 to 20 carbon atoms, and c is an integer of 2 or more, D(R$^7$)$_3$  [Chemical Formula 4]

wherein D is aluminium or boron, R$^7$ is hydrocarbyl having 1 to 20 carbon atoms or halogen-substituted hydrocarbyl having 1 to 20 carbon atoms,

[L-H]$^+$[Q(E)$_4$]$^-$  [Chemical Formula 5]

wherein L is a neutral Lewis base, [L-H]$^+$ is a Bronsted acid, Q is boron or aluminium in the +3 oxidation state, E is each independently an aryl group having 6 to 20 carbon atoms or an alkyl group having 1 to 20 carbon atoms in which one or more hydrogen atoms are substituted or unsubstituted with halogen, hydrocarbyl having 1 to 20 carbon atoms, an alkoxy functional group or a phenoxy functional group.

10. The catalyst system for ethylene oligomerization of claim 5, further comprising a support.

11. The catalyst system for ethylene oligomerization of claim 10, wherein the organic chromium compound and the cocatalyst are included in an amount of about 0.5 to about 20 parts by weight, and about 1 to about 1,000 parts by weight, respectively, based on 100 parts by weight of the support.

12. The catalyst system for ethylene oligomerization of claim 10, wherein the support includes hydroxyl groups and siloxane groups on the surface.

13. The catalyst system for ethylene oligomerization of claim 10, wherein the support includes one or more selected from the group consisting of silica, silica-alumina and silica-magnesia.

14. An ethylene oligomerization method comprising:
oligomerizing ethylene in the presence of the catalyst system for ethylene oligomerization of claim 5.

15. A preparation method of a catalyst system for ethylene oligomerization, comprising the steps of:
supporting a cocatalyst on a support; and
supporting an organic chromium compound represented by the following Chemical Formula 2 on the cocatalyst-supported support:

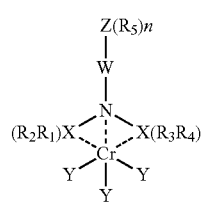

[Chemical Formula 2]

wherein X is phosphorus, arsenic or antimony;
W is ethylene or propylene;
R$_1$, R$_2$, R$_3$ and R$_4$ are each independently hydrocarbyl;
Z is nitrogen;
R$_5$ is hydrocarbyl;
Y is each independently halogen, hydrogen, or hydrocarbyl having 1 to 4 carbon atoms; and
n is 2.

16. The preparation method of claim 15, wherein the cocatalyst is one or more selected from the group consisting of the compounds represented by the following Chemical Formulae 3 to 5:

—[Al(R$^6$)—O]$_c$-  [Chemical Formula 3]

wherein R$^6$ is the same as or different from each other, and each independently a halogen radical, a hydrocarbyl radical having 1 to 20 carbon atoms, a halogen-substituted hydrocarbyl radical having 1 to 20 carbon atoms, and c is an integer of 2 or more, D(R$^7$)$_3$  [Chemical Formula 4]

wherein D is aluminium or boron, R$^7$ is hydrocarbyl having 1 to 20 carbon atoms or halogen-substituted hydrocarbyl having 1 to 20 carbon atoms,

[L-H]$^+$[Q(E)$_4$]$^-$  [Chemical Formula 5]

wherein L is a neutral Lewis base, [L-H]$^+$ is a Bronsted acid, Q is boron or aluminium in the +3 oxidation state, E is each independently an aryl group having 6 to 20 carbon atoms or an alkyl group having 1 to 20 carbon atoms in which one or more hydrogen atoms are substituted or unsubstituted with halogen, hydrocarbyl having 1 to 20 carbon atoms, an alkoxy functional group or a phenoxy functional group.

17. The preparation method of claim 15, wherein the organic chromium compound and the cocatalyst are included in an amount of about 0.5 to about 20 parts by weight, and about 1 to about 1,000 parts by weight, respectively, based on 100 parts by weight of the support.

18. The preparation method of claim 15, wherein the support includes one or more selected from the group consisting of silica, silica-alumina and silica-magnesia.

19. A preparation method of a catalyst system for ethylene oligomerization, comprising the steps of:
supporting an organic chromium compound represented by the following Chemical Formula 2 on a support; and
supporting a cocatalyst on the organic chromium compound-supported support:

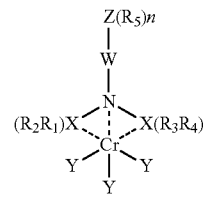

[Chemical Formula 2]

wherein X is phosphorus, arsenic or antimony;
W is ethylene or propylene;
R$_1$, R$_2$, R$_3$ and R$_4$ are each independently hydrocarbyl;
Z is nitrogen;
R$_5$ is hydrocarbyl;
Y is each independently halogen, hydrogen, or hydrocarbyl having 1 to 4 carbon atoms; and
n is 2.

* * * * *